United States Patent [19]

Togusari et al.

[11] Patent Number: 5,294,323
[45] Date of Patent: Mar. 15, 1994

[54] APPARATUS FOR GEL ELECTROPHORESIS

[75] Inventors: Teruo Togusari, Honjo; Kazuyuki Irisawa, Saitama; Hideki Kambara, Hachioji, all of Japan

[73] Assignees: Hitachi, Ltd.; Hitachi Electronics Engineering Co., Ltd., both of Tokyo, Japan

[21] Appl. No.: 69,841

[22] Filed: Jun. 1, 1993

[51] Int. Cl.⁵ .................... G01N 27/26; G01N 27/447
[52] U.S. Cl. .................... 204/299 R; 204/182.8; 356/344
[58] Field of Search .................... 204/299 R, 182.8; 356/344

[56] References Cited

U.S. PATENT DOCUMENTS

| | | | |
|---|---|---|---|
| 4,874,492 | 10/1989 | Mackay | 204/299 R X |
| 5,171,534 | 12/1992 | Smith et al. | 204/299 R X |
| 5,192,412 | 3/1993 | Kambara et al. | 204/182.8 X |

OTHER PUBLICATIONS

Biotechnology, vol. 9, Jul. 1991, "Real Time Automated Simultaneous Double-Stranded DNA Sequencing Using Two-Color Fluorophore Labeling", H. Kambara et al, pp. 648-651.
"BaseStation Automated DNA Sequence" brochure, 1991, Millipore Corporation, Bedford, Mass.

*Primary Examiner*—John Niebling
*Assistant Examiner*—John S. Starsiak, Jr.
*Attorney, Agent, or Firm*—Fay, Sharpe, Beall, Fagan, Minnich & McKee

[57] ABSTRACT

In an apparatus for gel electrophoresis in which a sample of fluorophore-labelled DNA fragments is caused to migrate by electrophoresis through a gel electrolyte layer in an electrophoresis plate from top to bottom, thereby separating the sample into individual DNA fragments, and a laser beam is launched horizontally into said electrolyte layer from one side of the electrophoresis plate in a direction perpendicular to the longitudinal axis of said electrophoresis plate, with the emitted fluorescences being detected to determine the base sequences of the respective DNAS, a mirror for reflecting fluorescences is provided at the back of the electrophoresis plate in such a way that it is parallel to the direction of laser beam application, and the fluorescences reflected by this mirror are received by a fluorescence detector such as a CCD sensor or MOS linear image sensor. In one embodiment, the mirror is inclined by an angle of 45° with the electrophoresis plate in such a way that it reflects the incident fluorescences upward, and the fluorescence detector is positioned above the mirror along the electrophoresis plate. In another embodiment, Texas Red having an excitation maximum wavelength of 596 nm and an emission maximum wavelength of 615 nm is used as the fluorophore and a He-Ne laser operating at a wavelength of 594 nm is used as the light source.

7 Claims, 4 Drawing Sheets

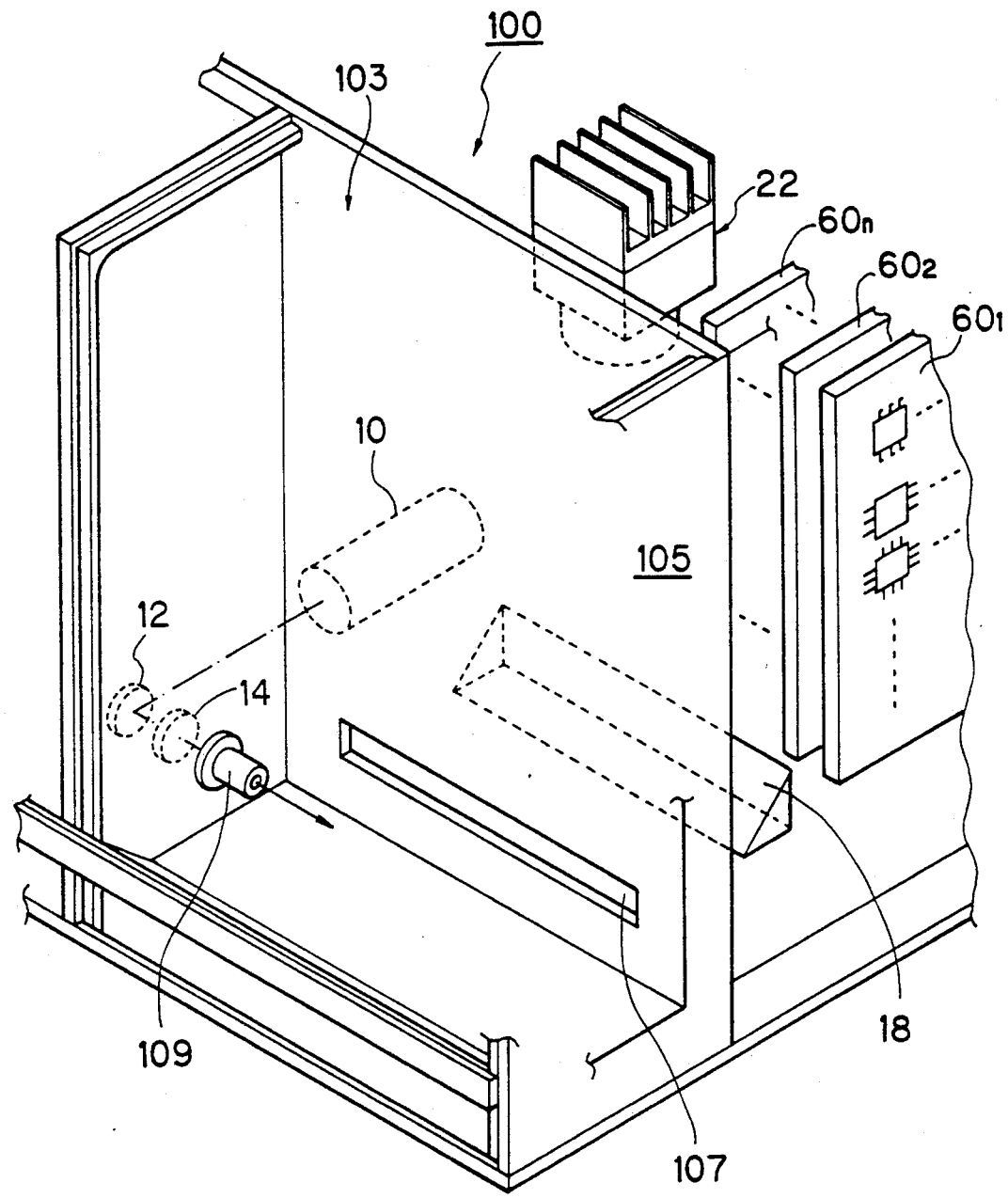

APPARATUS FOR GEL ELECTROPHORESIS

BACKGROUND OF THE INVENTION

This invention relates to an apparatus for electrophoresis. More particularly, this invention relates to a compact vertical-type apparatus for gel electrophoresis.

Gel electrophoresis is practiced extensively as a technique for determining the base sequences of DNA and other proteins. Conventionally, the sample to be subjected to electrophoresis is labelled with a radioisotope for analysis but this method has had the problem of being painstaking and time-consuming. Furthermore, the use of radioactive substances always calls for utmost safety and management and analysis cannot be performed in areas other than facilities that clear certain regulations. Under the circumstances, a method that uses fluorophores to label the sample and which detects fluorescences as emitted upon irradiation with light is being reviewed.

In this method, fluorophore-labelled DNA fragments are caused to migrate through a gel and a light excitation portion and a photodetector are provided for each electrophoresis track in an area 15–20 cm below the start point of electrophoresis. The DNA fragments are assayed as they pass through the line connecting the light excitation portion and the photodetector. A typical procedure of the method is described below. First, using as template the DNA chain to be determined for its base sequence, DNAs of various lengths with known terminal base species are replicated by a method involving an enzymatic reaction (the dideoxy method). Then, the replicated DNAs are labelled with a fluorophore. Stated more specifically, there are prepared a group of adenine (A) fragments, a group of cytosine (C) fragments, a group of guanine (G) fragments and a group of thymine (T) fragments, all being labelled with a fluorophore. A mixture of these fragment groups is injected into separate lane grooves in an electrophoretic gel and, thereafter, a voltage is applied at opposite ends of the gel. Since DNA is a chained polymer with negative charges, it will move across the gel at a rate in inverse proportion to its molecular weight. The shorter the DNA chain (the smaller its molecular weight), the faster will it move and vice versa; this is the principle behind the fractionation of DNA by molecular weight.

Japanese Laid-Open Patent Application (kokai) No. 21556/1988 teaches a DNA base sequencer that is adapted in such a way that a line on the gel in an apparatus for electrophoresis at which laser light is applied and the direction in which photodiodes are arranged are both perpendicular to the direction in which DNA fragments migrate in the apparatus. The setup of this apparatus is shown schematically in FIG. 6. An electrophoresis plate 74 comprises a gel (typically a polyacrylamide gel) held between two glass plates. The electrophoresis plate has an overall thickness of up to about 10 mm but the thickness of the gel electrolyte layer itself is less than about 1 mm. The upper end of the gel electrolyte layer is comb-shaped and located slightly below the upper end of the plate 74. Fluorophore-labelled DNA fragments to be assayed are injected into grooves 75 corresponding to the teeth of the comb.

In the apparatus shown in FIG. 6, a laser beam emitted from a light source 70 is reflected by a mirror 72 and launched horizontally from one side of the plate 74 at a predetermined point on the gel. As the fluorophore-labelled DNA fragments migrating through the gel pass through the irradiated region, they will fluoresce successively. The horizontal position of fluorescence emission tells the species of a particular terminal base, the time difference from the start of migration tells the length of a particular fragment, and the emission wavelength identifies the sample under assay. The fluorescence from each electrophoresis track is condensed by a lens 78 to focus at a light-receiving area in an image intensifier 80. The received signal is amplified and converted to an electric signal in a photodiode array 84 for the purpose of various measurements. The results of measurements are processed with a computer so that the sequences of the individual DNA fragments are calculated to determine the base sequence of the DNA at issue.

The conventional apparatus for gel electrophoresis uses an argon laser as a light source and adopts an image intensifier camera in the light-receiving optics. The image intensifier camera is not only very expensive but also comparatively large as an optical device. The argon laser is also of a comparatively large size and requires a large transformer for use with the associated drive power supply. As a result, the overall size of the conventional apparatus for electrophoresis becomes bulky, often making it difficult to allow for a space for accommodating signal processing boards and other related devices.

SUMMARY OF THE INVENTION

The present invention has been accomplished under these circumstances and has as an object providing an apparatus for gel electrophoresis in which a sample of fluorophore-labelled DNA fragments is caused to migrate by electrophoresis through a gel electrolyte layer in an electrophoresis plate from top to bottom, thereby separating the sample into individual DNA fragments, and a laser beam is launched horizontally into said electrolyte layer from one side of the electrophoresis plate in a direction perpendicular to the longitudinal axis of said electrophoresis plate, with the emitted fluorescences being detected to determine the base sequences of the respective DNAs. This apparatus is characterized in that a mirror for reflecting fluorescences is provided at the back of the electrophoresis plate in such a way that it is parallel to the direction of laser beam application, and that the fluorescences reflected by this mirror are received by a fluorescence detector.

In one embodiment of the present invention, the mirror is inclined by an angle of about 45° with the electrophoresis plate in such a way that it reflects the incident fluorescences upward, and the fluorescence detector is positioned above the mirror along the electrophoresis plate.

In another embodiment of the present invention, Texas Red having an excitation maximum wavelength of 596 nm and an emission maximum wavelength of 615 nm is used as the fluorophore and a He-Ne laser operating at a wavelength of 594 nm is used as the light source.

In the apparatus of the present invention, the fluorescence detector is installed in a vertical attitude, so it permits more efficient use of a limited available space than the conventional apparatus in which the fluorescence detector is installed in a horizontal attitude. The extra space that has become available as a result of installing the fluorescence detector in a vertical attitude can be used to lay out signal processing boards and other necessary devices.

In a preferred embodiment, the fluorescence detector is solely composed of a solid-state imaging device in place of the heretofore used light detector adopting an image intensifier and, in addition, a He-Ne laser is used in place of the conventionally used Ar laser. This is effective not only in reducing the overall size of the apparatus but also in realizing a substantial drop in the cost.

BRIEF DESCRIPTION OF THE DRAWINGS

FIG. 4 is a perspective view showing schematically the essential part of the measurement compartment in an example of the apparatus for gel electrophoresis that has the optics shown in FIG. 1;

THE PREFERRED EMBODIMENTS OF THE INVENTION

The apparatus for gel electrophoresis of the present invention is described below in greater detail with reference to FIGS. 1-5.

Figure 1:
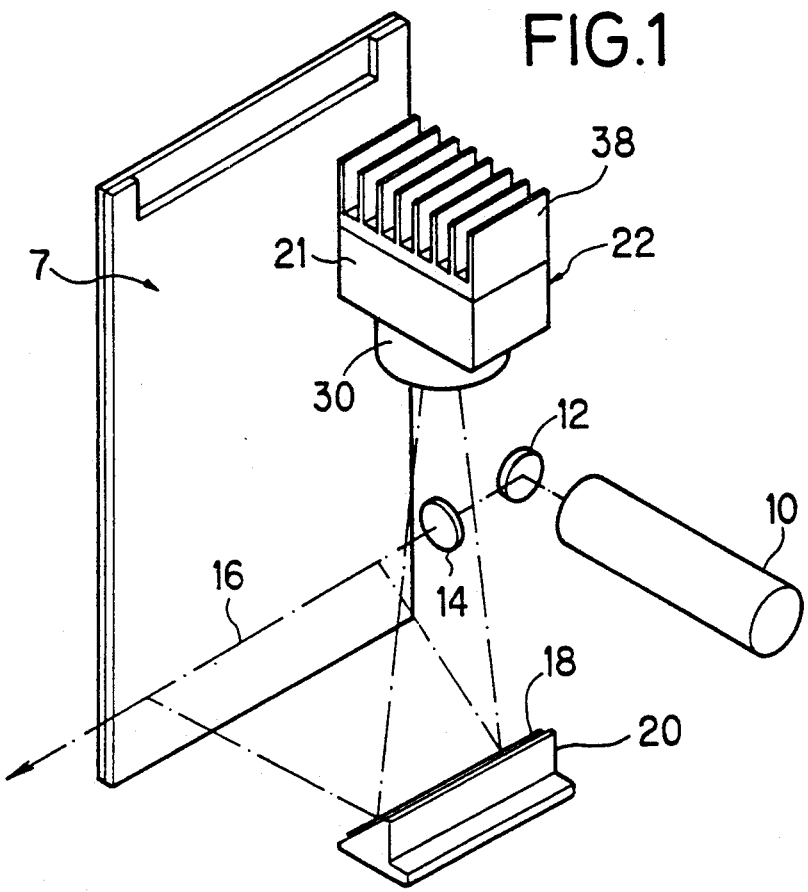
FIG. 1 is a sketch showing the layout of optics in the apparatus for gel electrophoresis of the present invention.

FIG. 1 is a perspective view showing schematically the essential part of an example of optics in the apparatus for gel electrophoresis of the present invention. A laser beam issuing from a light source 10 (such as a He-Ne laser operating at a wavelength of 594 nm) is reflected by a mirror 12 and focused by a condenser lens 14 so that it is launched into the gel electrolyte layer in an electrophoresis plate 7. When the laser light strikes a fluorophore-labelled DNA fragment as it migrates through the gel electrolyte layer, fluorescence is emitted from that fragment. The emitted fluorescence falls on a mirror 18 that is provided at the back of the electrophoresis plate and in a direction parallel to a linear irradiation region 16. The fluorescence is reflected upward by the mirror 18 and launched into a fluorescence detector 22 positioned just above the mirror 18. The fluorescence detector 22 consists of an enclosure 21 accommodating a solid-state imaging device (to be described below) and a Peltier device, as well as an imaging lens 30 mounted on the underside of the enclosure, and a heat sink 38 mounted on the top of the enclosure.

Laser is closely related to the reagent for effecting fluorophore labelling. The apparatus for gel electrophoresis of the present invention uses Texas Red (excitation maximum wavelength: 596 nm; emission maximum wavelength: 615 nm) as a fluorescent dye; hence, the light source 10 must be a He-Ne laser operating at 594 nm. This laser measures 425 mm long by 44 mm in diameter and it weighs 1.5 kg. Thus, the laser is much smaller and lighter than the conventional Ar laser and it costs no more than a third of the Ar laser, whereby it contributes a lot to the reduction in the overall size and cost of the apparatus. If the labelling fluorophore permits, a semiconductor laser may be used.

The fluorescence reflecting mirror 18 is in no way limited in terms of its material and shape. A planar mirror may be secured to an appropriate support member 20 or, alternatively, one surface of a support member 20 may be worked to provide a light-reflecting surface. In the embodiment shown in FIG. 1, the mirror 18 is inclined about 45° with the electrophoresis plate so that it reflects the incident fluorescence upward. Desirably, the mirror 18 has the necessary and sufficient length to insure that the fluorescences from a predetermined number of pixels (say, 512 pixels) that are arranged to span opposite ends of the linear irradiation region 16 of the electrophoresis plate will be reflected upward in one action.

Figure 2:
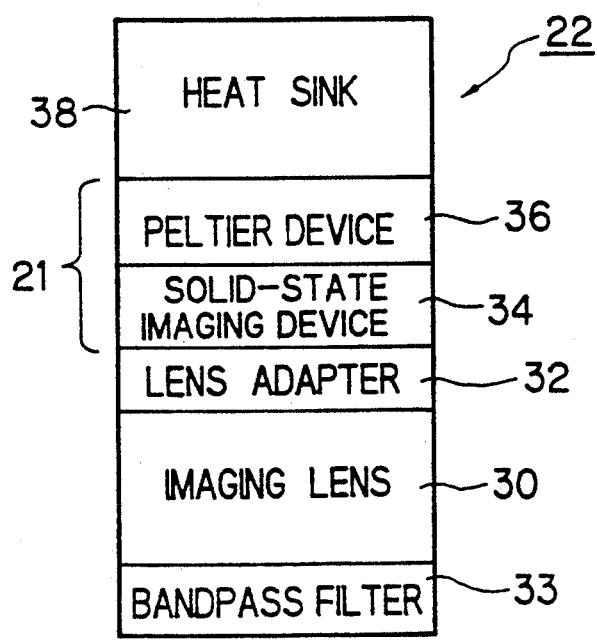
FIG. 2 is a schematic diagram showing the composition of the fluorescence detector used in the apparatus for gel electrophoresis of the present invention.

The composition of the fluorescence detector 22 is shown schematically in FIG. 2. The underside of the detector 22 (namely, the side facing the reflecting mirror 18) is fitted with the imaging lens 30, which is mounted on the enclosure 21 by means of a lens adapter 32. A bandpass filter 33 is attached to the distal end of the imaging lens 30. The bandpass filter 33 will cut off light at all wavelengths other than a desired one. A solid-state imaging device 34 such as a photodiode array, a CCD sensor or a MOS linear image sensor is provided in alignment with the optical axis of the imaging lens 30. As the temperature rises, an increasing amount of dark current will flow through the solid-state imaging device 34 and thereby reducing its S/N ratio. To avoid this problem, the solid-state imaging device 34 is adapted to be cooled with the Peltier device 36 so that it will be operating at all times at a predetermined temperature, say, in the range from 5 to 10° C. To enhance the cooling efficiency, the heat sink 38 is provided at the top of the enclosure 21. Both the solid-state imaging device 34 and the Peltier device 36 are included within the enclosure 21 which has an air-tight structure.

The solid-state imaging device is about four orders of magnitude less sensitive than the conventional photodetector using an image intensifier. To compensate for this low sensitivity of the solid-state imaging device, the present invention adopts the following four design features: (1) the solid-state imaging device is held at a sufficiently low temperature to cut off noise due to the dark current, thereby improving the S/N ratio; (2) the laser light operating at a wavelength of 594 nm is used to cut off the background light from the polyacrylamide gel; (3) in the case of an image intensifier, DNF fragments and fluorophore have been used at approximate concentrations of 0.03 picomole but with the solid-state imaging device, the concentrations of DNA fragments and fluorophore to be used are increased to about 0.1–0.15 picomole; and (4) in the case of an image intensifier, the time of single detection of fluorescence has been only 50 milliseconds but with the solid-state imaging device, the time is prolonged up to 2.7 seconds.

Figure 3:
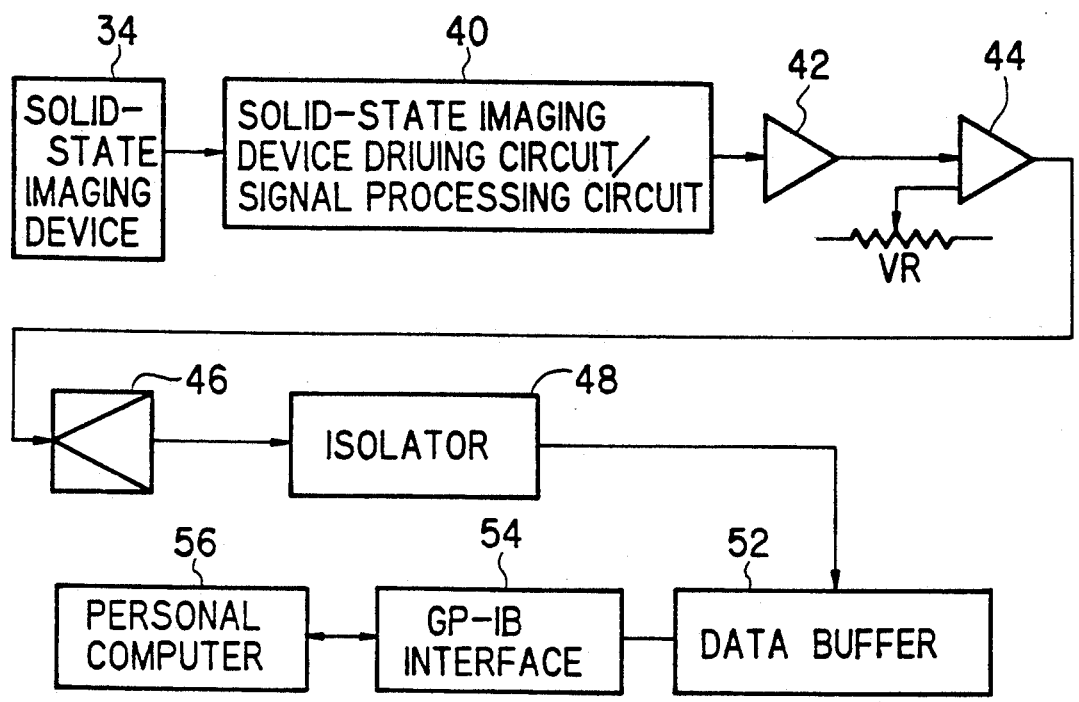
FIG. 3 is a block diagram showing the signal processing circuit in the fluorescence detector.
Figure 6:
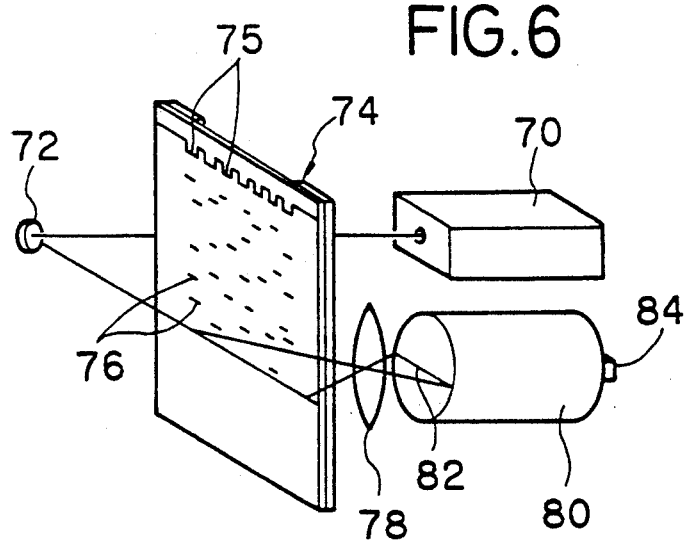
FIG. 6 is a sketch showing schematically the setup of the DNA base sequencer disclosed in Japanese Laid-Open Patent Application (kokai) No. 21556/1988.

FIG. 3 is a block diagram of the circuit used in the fluorescence detector for processing detection signals. Fluorescence received by the solid-state imaging device 34 passes through the combination circuit 40 for driving the solid-state imaging device and performing signal processing and, thence, supplied into a low-pass filter 42, where frequency components higher than 100 kHz are rejected. Further, the signal is passed through an amplifier 44 where it is amplified by a factor of 3 to cut off noise due to the dark current. The critical cutoff value is set by a variable resistor (VR). Thereafter, the analog signal is sent to an A/D converter 46, where it is converted to a 12-bit digital signal for sending to an isolator 48. The digital signal supplied from the isolator 48 is transformed to GP-IB data format in a data buffer 52. The data buffer 52 is connected to a control unit 56 such as a personal computer via a GP-IB interface 54.

FIG. 4 is a perspective view showing schematically the essential part of an example of the apparatus for gel electrophoresis that has the optics shown in FIG. 1. As shown, the apparatus generally indicated by 100 has a measurement compartment 103 that can be made completely dark for performing the necessary measurement. A slit 107 for admitting fluorescence is open in an area near the bottom of the rear wall 105 of the compartment 103. A fluorescence reflecting mirror 18 is positioned behind the rear wall 105 adjacent the slit 107. Signal processing boards $60_1, 60_2, \ldots$ and $60_n$ are positioned adjacent the fluorescence reflecting mirror 18 and the fluorescence detector 22. In the conventional apparatus, that space has been occupied by the fluorescence detector, so it has been necessary to position signal processing boards above the detector.

Further reference is made to FIG. 4. A laser light emitting end 109 is positioned near the bottom of one side wall of the measurement compartment 103. A laser beam generator 10 can also be provided behind the rear wall 105. The optical axis of the laser beam generator 10 is in alignment with those of the laser beam reflecting mirror 12, condenser lens 14 and the laser beam emitting end 109. The optical path of laser light issuing from the laser light emitting end 109 is preferably in substantial alignment with the longitudinal axis passing through the center of the slit 107.

Figure 5:
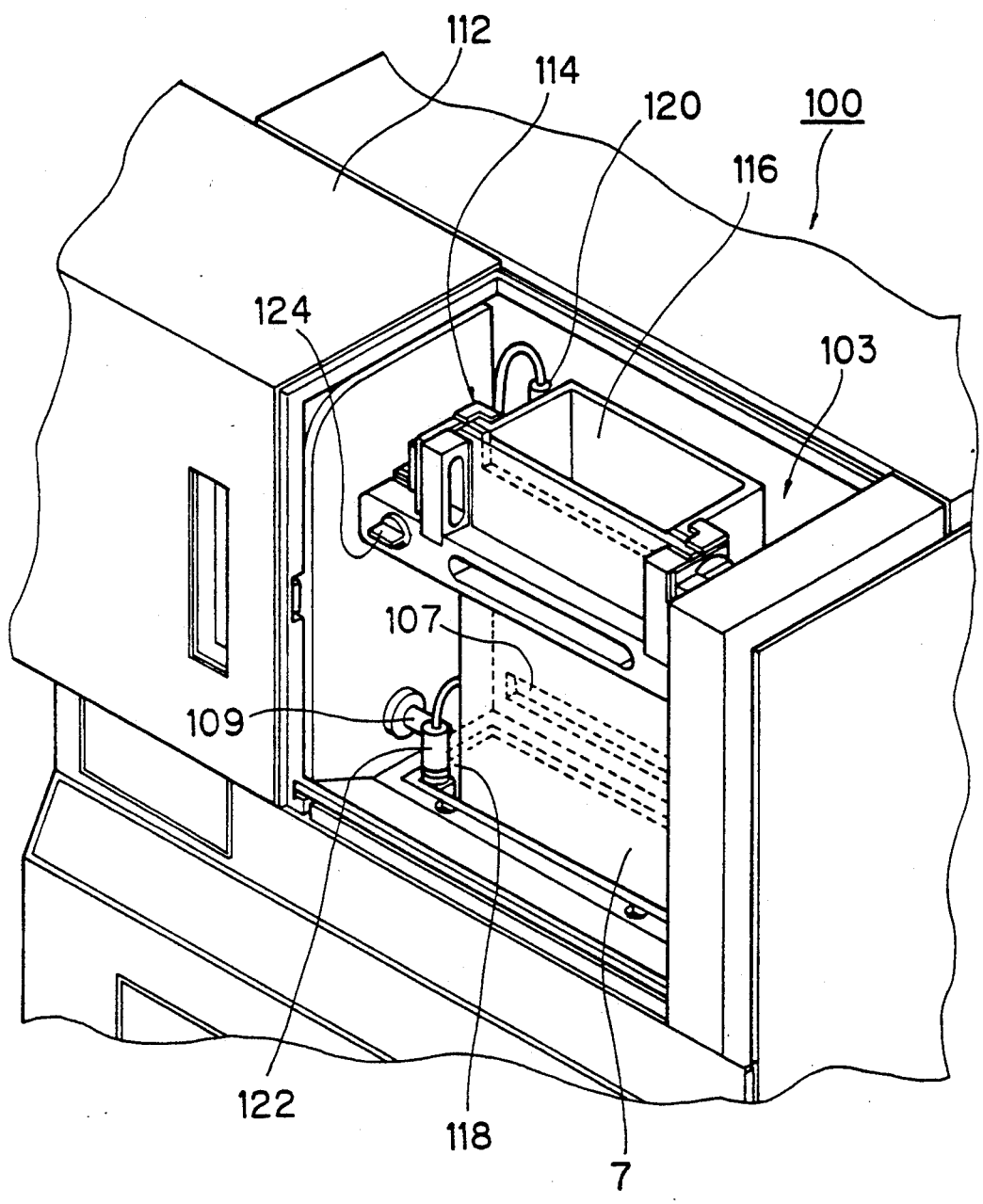
FIG. 5 is a perspective view showing schematically the essential part of the measurement compartment shown in FIG. 4 as it is fitted with an electrophoresis plate and buffer tanks.

FIG. 5 is a perspective view showing the essential part of the apparatus shown in FIG. 4, except that it has an electrophoresis plate set in an operative state. A slidable door 112 is provided in front of the measurement compartment 103. Before starting measurement, the door is closed to keep off light from entering the compartment 103, whereby it becomes completely dark. The electrophoresis plate indicated by 7 is retained in a vertical attitude within the compartment 103 by means of a plate holder 114. Buffer tanks 116 and 118 are provided at the top and bottom of the holder 114 and they contain the buffer solution that is necessary to perform gel electrophoresis. The top and bottom ends of the electrophoresis plate 7 are submerged in the buffer solution in the buffer tanks 116 and 118, respectively. To provide a current path starting at the buffer solution in the top tank and passing through the gel electrolyte layer in the electrophoresis plate to reach the buffer solution in the lower tank, electrodes 120 and 122 are fitted on the top and lower fubber tanks, respectively. A clamp mechanism 124 is provided to insure that the electrophoresis plate 7 can be disengaged from the holder 114 as required. The laser light emitting end 109 is positioned in such a way that its optical axis is in registry with the horizontal direction of the gel electrolyte layer in the electrophoresis plate.

What is claimed is:

1. In an apparatus for gel electrophoresis in which a sample of fluorophore-labelled DNA fragments is caused to migrate by electrophoresis through a gel electrolyte layer in an electrophoresis plate in a first direction, thereby separating the sample into individual DNA fragments, and laser light is launched into a linear irradiation region of said gel electrolyte layer in a second direction which is generally perpendicular to said first direction with the emitted fluorescence being detected to determine the base sequence of the particular DNA, the improvement wherein a mirror for reflecting fluorescence is provided at the back of the electrophoresis plate in such a way that it is parallel to said linear irradiation region and the fluorescence reflected from said mirror is received by a separate fluorescence detector composed of a solid-state imaging device.

2. An apparatus for gel electrophoresis according to claim 1 wherein said fluorophore is Texas Red having an excitation maximum wavelength of 596 nm and an emission maximum wavelength of 615 nm, and a He-Ne laser operating at a wavelength of 594 nm is used as a laser light source.

3. An apparatus for gel electrophoresis according to claim 1 wherein said mirror is inclined by an angle of about 45° with the electrophoresis plate so that it reflects the incident fluorescence upward, and said fluorescence detector is positioned above said mirror along the electrophoresis plate.

4. An apparatus for gel electrophoresis according to claim 1 wherein said mirror has the necessary and sufficient length to insure that the fluorescences from a predetermined number of pixels that are arranged to span opposite ends of the linear irradiation region of the electrophoresis plate will be reflected upward in one action.

5. An apparatus for gel electrophoresis according to claim 1 wherein said solid-state imaging device is a CCD sensor or a MOS linear image sensor and is cooled with a mechanism composed of a Peltier device.

6. An apparatus for gel electrophoresis according to claim 1 wherein signal processing boards are provided adjacent said mirror and said fluorescence detector.

7. An apparatus for gel electrophoresis according to claim 1 wherein DNA fragments of a concentration within the range from 0.1 to 0.15 picomole and fluorophore of a concentration within the range from 0.1 to 0.15 picomole are injected into grooves associated with individual electrophoresis lanes.

* * * * *